(12) United States Patent
Chuter (10) Patent No.: US 9,486,347 B2
(45) Date of Patent: Nov. 8, 2016

(54) BALLOON CATHETERS AND SYSTEMS AND METHODS FOR DELIVERING STENTS USING SUCH CATHETERS

(71) Applicant: Timothy A. M. Chuter, San Francisco, CA (US)

(72) Inventor: Timothy A. M. Chuter, San Francisco, CA (US)

(*) Notice: Subject to any disclaimer, the term of this patent is extended or adjusted under 35 U.S.C. 154(b) by 137 days.

(21) Appl. No.: 14/133,542

(22) Filed: Dec. 18, 2013

(65) Prior Publication Data

US 2015/0216691 A1   Aug. 6, 2015

(51) Int. Cl.
*A61F 2/06* (2013.01)
*A61F 2/958* (2013.01)
*A61F 2/82* (2013.01)

(52) U.S. Cl.
CPC .......... *A61F 2/958* (2013.01); *A61F 2002/826* (2013.01); *A61F 2002/9583* (2013.01)

(58) Field of Classification Search
CPC .......... A61F 2/958; A61F 11/00; A61F 2/06; A61F 2/84; A61M 25/10; A61M 25/104; A61M 27/00; A61B 17/0057; A61B 17/3207
See application file for complete search history.

(56) References Cited

U.S. PATENT DOCUMENTS

| | | | |
|---|---|---|---|
| 4,763,654 A | 8/1988 | Jang | |
| 5,226,880 A | 7/1993 | Martin | |
| 5,342,305 A | 8/1994 | Shonk | |
| 5,752,934 A | 5/1998 | Campbell et al. | |
| 6,024,722 A | 2/2000 | Rau et al. | |
| 6,187,014 B1 | 2/2001 | Goodin et al. | |
| 7,147,655 B2 | 12/2006 | Chermoni | |
| 2004/0098081 A1 | 5/2004 | Landreville et al. | |
| 2008/0154351 A1 | 6/2008 | Leewood et al. | |
| 2009/0299450 A1 | 12/2009 | Johnson et al. | |
| 2011/0034986 A1* | 2/2011 | Chou .................. | A61B 17/0057 623/1.11 |
| 2011/0077731 A1 | 3/2011 | Lee et al. | |
| 2011/0152997 A1 | 6/2011 | Kelly et al. | |

FOREIGN PATENT DOCUMENTS

| | | |
|---|---|---|
| EP | 0714640 A1 | 5/1996 |
| WO | 9638109 | 12/1996 |
| WO | 0195833 A2 | 12/2001 |

OTHER PUBLICATIONS

Korean Intellectual Property Office, International Search Report and Written Opinion of the International Searching Authority for corresponding International Application No. PCT/US2014/070990, Mar. 24, 2015, 14 pages.

* cited by examiner

*Primary Examiner* — Victor Nguyen
(74) *Attorney, Agent, or Firm* — Willaim A. English; Vista IP Law Group LLP (57) ABSTRACT

Apparatus and methods are provided for treating lesions within a blood vessel include a two-layer angioplasty balloon designed for the simultaneous deployment of multiple balloon-expanded stents. The high-compliance (elastic) outer balloon secures stent position. The low-compliance (inelastic) inner balloon drives angioplasty and stent expansion. Stent deployment starts with the injection of a small quantity of fluid into the outer balloon, which bulges slightly at both ends and into the spaces between the stents and, once the stent has expanded a little, between the struts of the stents. The injection port to the outer balloon is then closed, and fluid is injected only into the inner balloon, which expands, opening the stents.

20 Claims, 4 Drawing Sheets

BALLOON CATHETERS AND SYSTEMS AND METHODS FOR DELIVERING STENTS USING SUCH CATHETERS

FIELD OF THE INVENTION

The present invention relates generally to apparatus and methods for treating stenoses, occlusions, or other lesions within a body lumen, such as an artery or other blood vessel, and, more particularly, to balloon catheters for delivering stents, and to systems and methods for treating lesions within body lumens.

BACKGROUND

Tubular endoprosthesis or "stents" have been suggested for dilating or otherwise treating stenoses, occlusions, and/or other lesions within a patient's vasculature or other body lumens. For example, a self-expanding stent may be maintained on a catheter in a contracted condition, e.g., by an overlying sheath or other constraint, and delivered into a target location, e.g., a stenosis within a blood vessel or other body lumen. When the stent is positioned at the target location, the constraint may be removed, whereupon the stent may automatically expand to dilate or otherwise line the vessel at the target location.

Alternatively, a balloon-expandable stent may be carried on a catheter, e.g., crimped or otherwise secured over a balloon, in a contracted condition. When the stent is positioned at the target location, the balloon may be inflated to expand the stent and dilate the vessel.

Balloon-expanded stents tend to be relatively stiff and straight, as are the balloons used to deliver them, which reduces the ability of the stents to conform to the shape of vessels that are curved and/or angulated. Curved connectors between rings of certain stent designs may allow bending of the unexpanded stent, but such connectors rarely provide enough differential lengthening to allow significant bending of the expanded stent because the connectors are made from the same inelastic material used throughout the stent. Moreover, if such a fully expanded stent were capable of bending easily, e.g., to accommodate a bend in the artery, the stent may be capable of bending repeatedly in response to arterial motion, increasing risk of the stent becoming work-hardened and/or breaking, e.g., after deployment within a body lumen, such as a cardiac vessel, within which the stent may experience significant dynamic forces. The interface between the end of a substantially stiff, straight balloon-expanded stent and a relatively soft, otherwise curved artery may also become the focus of stress. The resulting microtrauma may cause inflammation, scarring, and/or flow-limiting narrowing, especially when the artery stretches or bends repeatedly with the cardiac cycle, respiratory excursion, and/or flexion/extension of a joint.

One solution involves the implantation of many short unconnected stents, so that the stented artery can bend, just as a long train bends. The simultaneous delivery of multiple short balloon-expanded stents is complicated by the tendency of individual stents to migrate relative to the balloon during inflation. When a conventional balloon on a balloon catheter is expanded, one end of the balloon may initially expand before the other, which may cause the stent to migrate away from the initially expanding end and/or compress the stent axially, or both ends may expand initially before a central region carrying the stent, which may cause the stent to compress or otherwise deform undesirably. If this occurs, the actual position of the stent may be difficult to control, which risks the stent being deployed misaligned relative to a desired location. This aspect of balloon expansion may be particularly problematic when deploying many short stents.

Accordingly, an improved apparatus and methods for delivering stents would be useful.

SUMMARY OF THE INVENTION

The present invention is directed to apparatus and methods for treating stenoses, occlusions, or other lesions within a body lumen, such as an artery or other blood vessel. More particularly, the present invention is directed to apparatus and methods for delivering and expanding stents within a body lumen. The apparatus, systems, and methods described herein may involve simultaneous delivery of multiple stents and/or maintaining multiple stents in substantially stable positions relative to one another and a balloon over which the stents are mounted.

One solution described herein is to substitute a series of relatively short, independent stents for a single, relatively long stent. In this approach, the stents may function similar to cartilage rings of the trachea or the hoops of a dryer hose, e.g., maintaining luminal support without greatly reducing the flexibility of the overall stent/artery composite. Despite providing interrupted support, short stents may satisfy the patency requirements of a post-angioplasty artery, which may otherwise be prone to dissection and luminal compression from dilatation resistant plaque.

Most dissections spiral down the affected artery, and are connected to the main lumen by only one or two transverse tears in the intima. A short stent near the tear may be sufficient to interrupt flow through the entire dissection, and a series of short stents may interrupt any tendency of localized dissections to propagate down the artery. A series of short stents may also be equally effective at dealing with the usual rigid atherosclerotic plaque, which, like a tabletop, does not need continuous support throughout its length.

Balloon-expanded stents may have advantages over self-expanding stents, especially when multiple, relatively short stents are being delivered. A short balloon-expanded stent may be carried on the outer surface of the balloon to the arterial wall, which may aid in maintaining control over position and orientation of the stent(s) throughout delivery and deployment. The same is not true of a relatively short self-expanding stent, which may tend to jump and twist in the interval between release from a delivery sheath and/or other deployment within an artery.

Current balloon-expanded stents tend to suffer from the same problem: the stent and balloon cannot be attached securely to one another because they expand in different ways. The stents generally stretch, while the non-compliant balloons typically used to deliver them unfurl. Compliant balloons, on the other hand, are capable of stretching, just like a stent, but cannot withstand the pressures typically used for arterial dilatation and stent expansion.

The lack of a stable connection between the balloon and the balloon-expanded stent is compounded by a phenomenon called "dog-boning," in which a non-compliant balloon opens first at the ends where there is no stent to impede expansion. Expansion at the ends may continue until they reach full diameter, whereupon expansion may progress from the ends towards the middle of the balloon. Multiple, short stents may be pushed down the resulting sloped surface of the balloon towards the middle of the balloon, where they may collide and expand, without the intended spacing. The apparatus and methods described herein may substantially maintain desired spacing of multiple spaced-apart stents during delivery and/or expansion.

For example, in one aspect, the apparatus and methods herein combine the pressure tolerance of an internal low-compliance (high-pressure) balloon with the elasticity of an external high-compliance (low-pressure) balloon. Optionally, saline or other fluids and/or lubricious (e.g., hydrogel) coatings between the two balloons, may facilitate the balloons sliding relative to one another, and/or may facilitate the outer balloon conforming to irregularities on the inner surface of the stent(s) delivered by the balloons, which may ensure that the two stay together throughout expansion.

In accordance with one embodiment, a system is provided for treating a body lumen that includes an elongate tubular member including a proximal end, a distal end sized for introduction into a body lumen, and a first inflation lumen extending between the proximal and distal ends; an inner balloon on the distal end formed from substantially inelastic material defining a central region, the inner balloon expandable from a delivery configuration in which the inner balloon is rolled or folded around the distal end, and an enlarged configuration in which the central region defines a substantially uniform diameter when inflation media is introduced into the first inflation lumen; and an outer balloon on the distal end overlying the inner balloon, the outer balloon formed from elastic material such that the outer balloon expands elastically when the inner balloon is expanded from the contracted configuration to the enlarged configuration.

Optionally, at least one of the inner and outer balloons include one or more features to prevent substantial transfer of non-radial forces generated, when the inner balloon expands from the contracted configuration to the enlarged configuration, to be transferred to the outer balloon. In exemplary embodiments, the one or more features may include one or more of lubricious fluid disposed within a space between the inner and outer balloons, a lubricious outer surface of the inner balloon, a lubricious inner surface of the outer balloon, e.g., by applying a lubricious coating to one or both surfaces and/or forming one or both balloons from lubricious material, and the like.

A single stent may be disposed around the outer balloon over at least a portion of the central region of the inner balloon, or a plurality of stents may be disposed around the outer balloon and spaced apart from one another and aligned over the central region of the inner balloon. Optionally, the outer balloon may include one or more features on the outer surface thereof that engage the stent(s) to prevent migration of the stent(s) relative to the outer balloon.

In accordance with another embodiment, an apparatus for treating a body lumen is provided that includes an elongate tubular member including a proximal end, a distal end sized for introduction into a body lumen, and a first inflation lumen extending between the proximal and distal ends; an inner balloon on the distal end and including first and second ends attached to the distal end, the inner balloon formed from substantially inelastic material and having an interior communicating with the first inflation lumen such that a central region of the inner balloon expands to a substantially uniform diameter when inflation media is introduced into the first inflation lumen; an outer balloon on the distal end overlying the inner balloon, the outer balloon formed from elastic material, at least one of an inner surface of the outer balloon and an outer surface of the inner balloon comprising lubricious material such that the outer surface slidably engages the inner surface when the inner balloon is expanded; and a plurality of stents disposed around the outer balloon and spaced apart from one another and aligned over the central portion of the inner balloon.

In accordance with still another embodiment, an apparatus for treating a body lumen is provided that includes an elongate tubular member including a proximal end, a distal end sized for introduction into a body lumen, and first and second inflation lumens extending between the proximal and distal ends; an inner balloon on the distal end and including first and second ends attached to the distal end, the inner balloon formed from substantially inelastic material and having an interior communicating with the first inflation lumen such that a central region of the inner balloon expands to a substantially uniform diameter when inflation media is introduced into the first inflation lumen; an outer balloon on the distal end overlying the inner balloon, the outer balloon formed from elastic material and having an interior communicating with the second inflation lumen for expanding the outer balloon independently of expansion of the inner balloon; and a plurality of stents disposed around the outer balloon and spaced apart from one another and aligned over the central region of the inner balloon.

In accordance with another embodiment, a method is provided for treating a lesion within a body lumen that includes providing a delivery catheter including inner and outer balloons on a distal end thereof, the inner balloon in a delivery configuration in which a central region of the inner balloon is rolled or folded around the distal end, and one or more stents mounted on the outer balloon over the central region of the inner balloon. The distal end may be introduced into a body lumen within the patient's body, and the inner balloon may be expanded to an enlarged configuration in which the inner balloon at least partially unrolls or unfolds, thereby radially expanding the outer balloon and the one or more stents thereon, wherein an interface between the inner and outer balloons prevents non-radial forces generated by the inner balloon as it unrolls or unfolds from being transferred to the one or more stents as they are expanded.

In accordance with yet another embodiment, a method for treating a patient is provided that includes providing a delivery catheter including inner and outer balloons on a distal end thereof, and a plurality of stents spaced apart from one another over central regions of the inner and outer balloons; introducing the distal end into a body lumen within the patient's body with the inner and outer balloons in a contracted condition; inflating the outer balloon to engage the stents without expanding the stents; and expanding the inner balloon to substantially simultaneously expand the stents and the outer balloon around the inner balloon, the inner balloon sliding relative to the outer balloon such that the outer balloon engages the stents to prevent substantial migration of the stents as the inner balloon expands.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It will be appreciated that the exemplary apparatus shown in the drawings are not necessarily drawn to scale, with emphasis instead being placed on illustrating the various aspects and features of the illustrated embodiments.

DETAILED DESCRIPTION OF THE EXEMPLARY EMBODIMENTS

Figure 1:
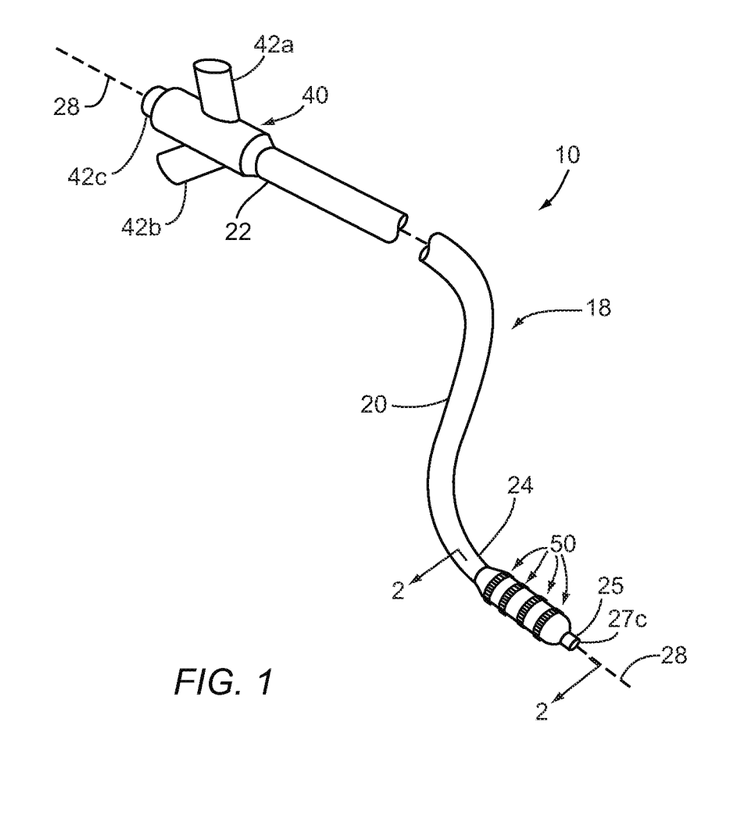
FIG. 1 is a perspective view of an exemplary embodiment of a balloon catheter carrying a plurality of independent stents.
Figure 2:
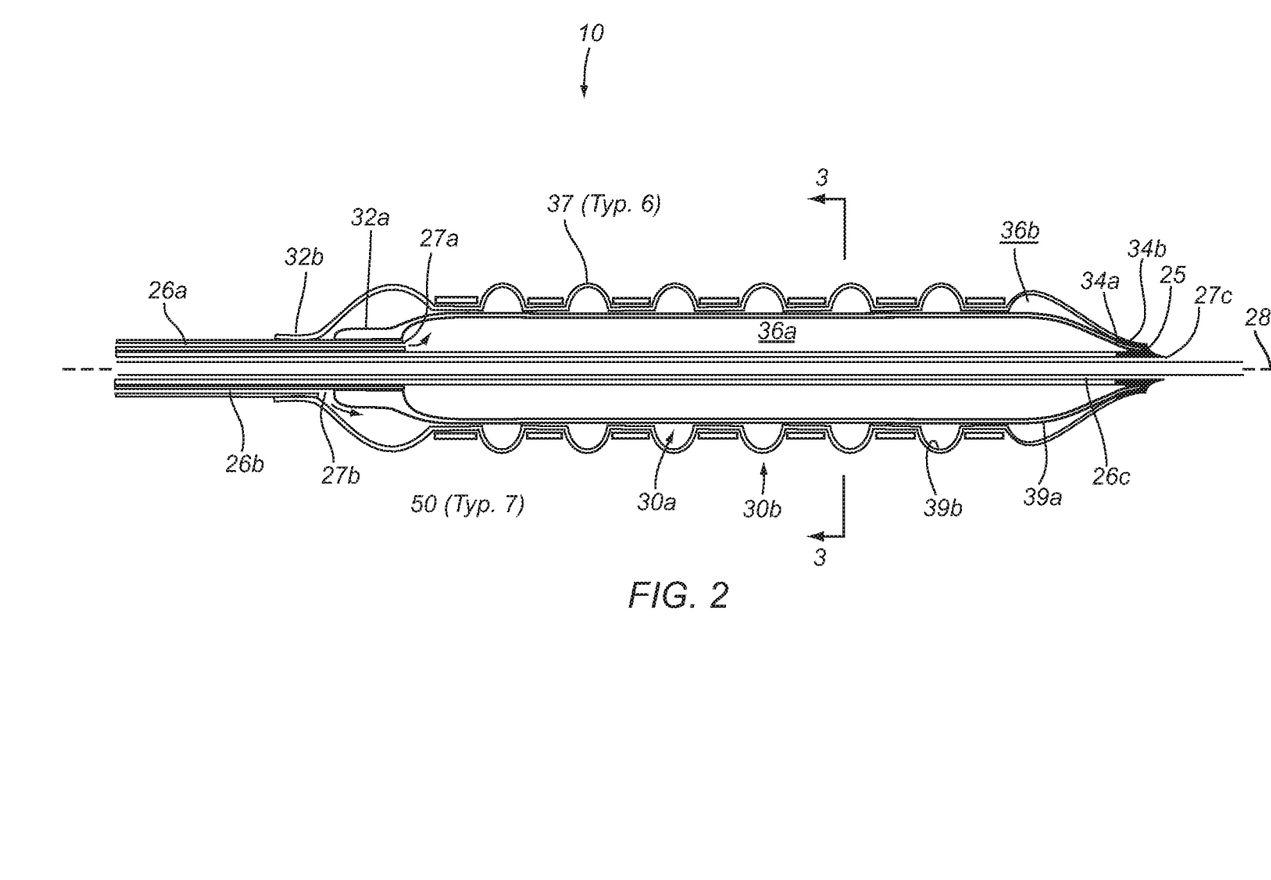
FIG. 2 is a longitudinal cross-sectional view of a distal portion of the balloon catheter of FIG. 1 taken along line 2-2 in FIG. 1.
Figure 3:
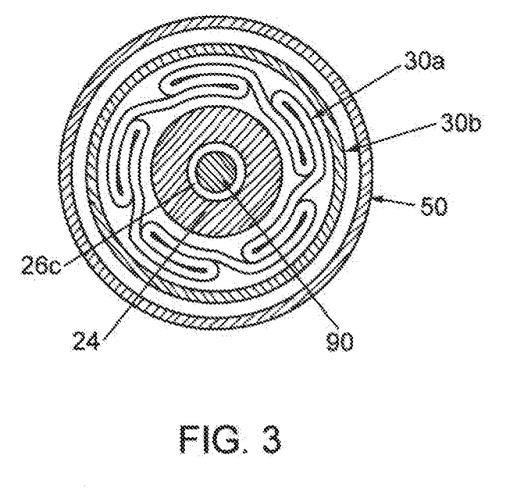
FIG. 3 is a cross-sectional view of the distal portion of the balloon catheter of FIG. 1 taken along line 3-3 in FIG. 2 with the balloons and stents in contracted or delivery conditions.

Turning to the drawings, FIGS. 1-3 show an exemplary embodiment of an apparatus 10 including a balloon catheter 18 and one or more stents 50 thereon, e.g., for delivering the stent(s) 50 into a body lumen and/or otherwise treating a lesion therein (not shown). As shown in FIG. 2, seven (7) spaced-apart independent stents 50 are shown carried on the balloon catheter 18, although it will be appreciated that any desired number of stents 50 may be provided, such as two, three, four, five, six, or more stents (not shown), as desired. Optionally, the apparatus 10 may be provided as part of a kit or system including one or more additional components, such as one or more syringes or other sources of inflation media, a guide catheter (not shown), and/or one or more guidewires (one guidewire 90 shown in FIG. 2).

Generally, as best seen in FIG. 1, the catheter 18 includes an elongate tubular member 20 having a proximal end 22, a distal end 24 sized for introduction into a patient's body, and one or more lumens 26 (best seen in FIG. 2) extending between the proximal and distal ends 22, 24, thereby defining a longitudinal axis 28 extending between the proximal and distal ends 22, 24. As shown, the catheter 18 may include a pair of concentric and/or overlapping balloons or other expandable members 30 on the distal end 24, e.g., a first or inner balloon 30a and a second or outer balloon 30b, for expanding the plurality of stents 50 carried thereon, as described further below. Optionally, the distal end 24 and/or the balloon(s) 30 may include one or more markers, e.g., one or more bands of radiopaque material (not shown), to facilitate positioning the catheter 18 within a patient's body, also as described further elsewhere herein.

The catheter 18 may be formed from one or more tubular bodies, e.g., having variable flexibility along its length, if desired. For example, the distal end 24 may be substantially flexible to facilitate introduction through tortuous anatomy, e.g., terminating in a rounded, tapered, and/or other substantially atraumatic distal tip 25. The proximal end 22 may be substantially flexible, semi-rigid, or rigid, e.g., having sufficient column strength to facilitate advancing the distal end 24 through a patient's vasculature by pushing on and/or otherwise manipulated the proximal end 2. The catheter 22 may be formed from plastic, metal, or composite materials, e.g., a plastic material having one or more wires, braids, or other reinforcement elements (not shown) embedded or otherwise provided within the wall of the catheter 18, which may prevent kinking and/or buckling of the catheter 18 during advancement or other manipulation.

As shown in FIG. 1, the catheter 18 may include a handle 40 on the proximal end 22, e.g., to facilitate manipulating the catheter 18. The handle 40 may include one or more ports 42 communicating with respective lumens 26 within the catheter 18, as described further below. The handle 40 may be molded, machined, or otherwise formed from plastic, metal, or composite material, e.g., providing an outer casing, which may be contoured or otherwise shaped to ease manipulation. The proximal end 22 of the catheter 18 may be attached to the handle 40, e.g., by bonding, cooperating connectors, interference fit, and the like.

In the exemplary embodiment shown in FIG. 2, the catheter 18 includes at least three lumens 26 extending between the proximal and distal ends 14, 16. For example, the catheter 18 may include inflation lumens 26a, 26b that extend from respective side ports 42a, 42b on the handle 40 through the catheter 18 to openings 27a, 27b that communicate with interiors 36a, 36b of respective balloons 30a, 30b. Alternatively, the second inflation lumen 26b and second side port 42b may be omitted, e.g., if the outer balloon 30b is not inflated independent of the inner balloon 30a, as described elsewhere herein. The side ports 42a, 42b on the handle 40 may include one or more connectors, e.g., a luer lock connector (not shown), one or more seals (also not shown), and the like. A source of inflation media and/or vacuum, e.g., a syringe filled with saline or other inflation media (not shown), may be connected to the side ports 42a, 42b, e.g., directly or via tubing (also not shown), for expanding and/or collapsing the balloons 30 independently of one another.

In addition, the catheter 18 may include an instrument lumen 26c that extends from port 42c on the handle 40 to an opening 27c in the distal tip 25. The instrument lumen 26c may have sufficient size to allow a guidewire or other rail or instrument (e.g., guidewire 90 shown in FIG. 2) to be inserted therethrough, e.g., to facilitate introducing the catheter 18 into a patient's body, as described further below. The port 42c may include one or more seals (not shown) in or adjacent the port 42c that prevent fluid, e.g., blood, from flowing proximally out of the port 42c, yet allow one or more instruments to be inserted therethrough and into the instrument lumen 26c. Alternatively, a "rapid exchange" instrument lumen may be provided that extends from the opening 27c to a proximal port (not shown) proximal to and/or closer to the balloons 30 than the handle 40.

As shown in FIG. 2, the lumens 26 may be concentric with one another, e.g., with inner lumen 26a communicating with the interior 36a of the inner balloon 30a and outer lumen 26b communicating with the interior 36b of the outer balloon 30b. Alternatively, the lumens 26 may be disposed in side-by-side and/or other arrangements (not shown) within the body of the catheter 18. In an alternative embodiment, the outer lumen 26b may be omitted, e.g., if the outer balloon 30b is not independently expandable, as described further elsewhere herein.

Returning to FIGS. 1 and 2, in the embodiment shown, the first or inner balloon 30a and second or outer balloon 30b on the distal end 24 are expandable independently of one another. For example, the ends 32, 34 of the balloons 30 may be bonded or otherwise secured to the distal end 24 of the catheter 18, e.g., by bonding with adhesive, sonic welding, using an annular collar or sleeve (not shown), and the like. The rest of the balloons 30 including central or main regions 38 remain substantially free and/or expandable relative to one another and the distal end 24.

As best seen in FIG. 2, the inner balloon 30a may include a proximal end 32a attached directly to the distal end 24 of the catheter 18 and a distal end 34a attached directly to the distal end 24 proximal to instrument lumen port 27c and/or otherwise adjacent the distal tip 25. The outer balloon 30b includes a first or proximal end 32b that extends at least partially over the proximal end 32a of the inner balloon 30a and a second or distal end 34b. For example, the proximal end 32b may be attached to the distal end 24 of the catheter body 20 proximal to the proximal end 32a of the inner balloon 30a and/or over the proximal end 32a itself. The distal end 34b of the outer balloon 30b may be attached over or adjacent to the distal end 34a of the inner balloon 30a, e.g., by bonding, sonic welding, using an annular collar or sleeve (not shown), and the like, as described elsewhere herein.

Figure 4:
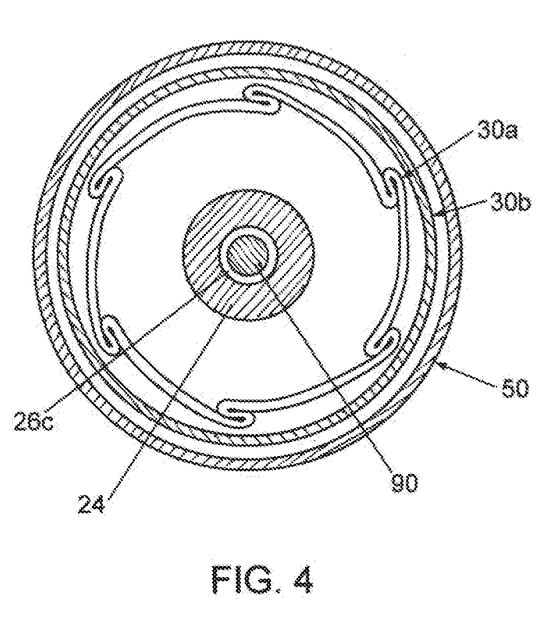
FIG. 4 is a cross-sectional view of the distal portion of the balloon catheter shown in FIG. 3 after partially expanding the balloons and stents.
Figure 5:
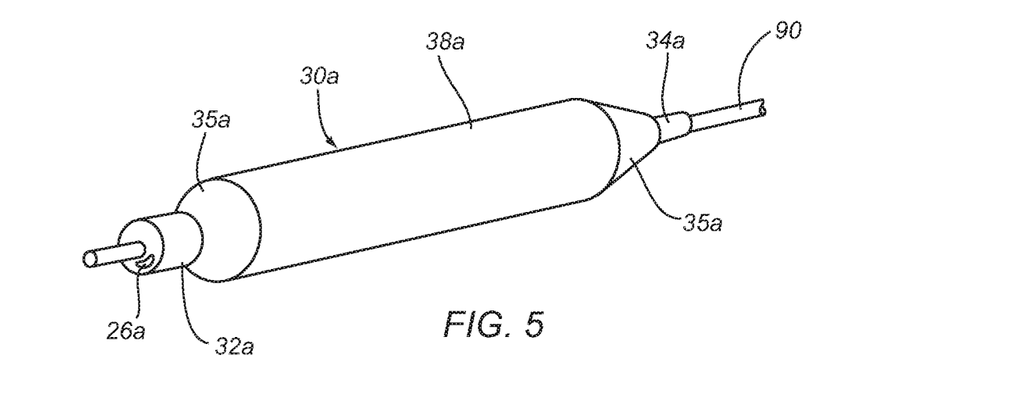
FIG. 5 is a perspective view of an exemplary embodiment of a balloon that may be provided as an inner balloon on the balloon catheter of FIG. 1.
Figure 6:
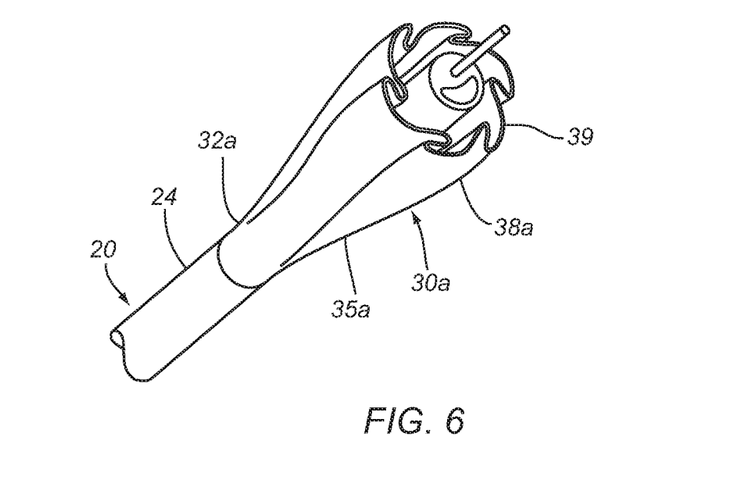
FIG. 6 is a detail of the balloon of FIG. 5 being folded about its periphery.

The inner balloon 30a may be expandable from a contracted or delivery condition (shown in FIG. 3) to an enlarged or dilation condition (shown in FIG. 4). In an exemplary embodiment, shown in FIG. 5, the inner balloon 30a may be shaped such that the central or main region 38a expands to a substantially uniform cylindrical shape in the enlarged condition, e.g., having a diameter between about two and nine millimeters (2-9 mm) when fully expanded, and a length between about ten and two hundred millimeters (10-200 mm). The inner balloon 30a may be at least partially rolled or folded, e.g., to define a plurality of folds 39 in the contracted condition, as shown in FIG. 6, e.g., to minimize a profile of the inner balloon 30a. On either side of the central region 38a, the inner balloon 30a may transition to the proximal and distal ends 32a, 34a. The proximal and distal transition portions 35a may have a frustoconical or other tapered shape, as shown, or may be substantially blunt (not shown).

For example, the inner balloon 30a may be formed from substantially inelastic or non-compliant material, e.g., PET, nylon, or mid to high durometer PEBAX, such that the inner balloon 30a expands to a predetermined size in its enlarged condition once sufficient fluid is introduced into the interior 36a of the balloon 30a. Thus, the inner balloon 30a may be expanded to a relatively high pressure, e.g., between about eight and twenty atmospheres (8-20 ATM), without substantial risk of rupturing, e.g., to apply sufficient pressure to expand and/or dilate the stent(s) 50 and/or dilate a lesion within which the balloons 30 are expanded, as described further below.

Similarly, the outer balloon 30b may also be expandable from a contracted condition (also shown in FIG. 3) to an enlarged condition (shown in FIG. 4). Unlike the inner balloon 30a, the outer balloon 30b may be formed from substantially elastic and/or compliant material, e.g., silicone, polyurethane, polyethylene, or low to mid durometer PEBAX, such that the outer balloon 30b may stretch as it is expanded to a variety of sizes, e.g., depending upon the volume and/or pressure of fluid within the interior 36b. Optionally, the outer balloon 30b may have a relaxed size smaller than the inner balloon 30a in its contracted condition, e.g., such that the outer balloon 30b is partially stretched over the inner balloon 30a when the outer balloon 30b is mounted on the distal end 24 of the catheter 18. Thus, the outer balloon 30b may initially be under some tension, which may help maintain the inner balloon 30a in the contracted condition, e.g., to prevent substantially unintended movement of the folds 39. Alternatively, the outer balloon 30b may have a relaxed size similar to or slightly larger than the inner balloon 30a in the contracted condition.

The outer balloon 30b may have a substantially uniform wall thickness, e.g., between the proximal and distal ends 32b, 34b. Alternatively, the wall thickness may vary, e.g., to provide one or more features on the central region 38b for engaging the stent(s) 50 carried thereon, as described elsewhere herein. For example, the outer balloon 30b may include relatively thin-walled regions, e.g., annular regions 37, spaced apart from one another such that the thin-walled regions 37 are disposed between the stents 50 loaded onto the outer balloon 30b. Thus, the stents 50 may be loaded onto relatively thick-walled regions of the outer balloon 30b, which may have greater resistance to stretching or otherwise expanding than the thin-walled regions 37.

In addition or alternatively, the outer balloon 30b may include a plurality of protrusions or indentations configured to substantially secure the stents 50 and/or substantially maintain the spacing of the stents 50, e.g., during introduction into a target body lumen and/or during expansion of the balloon(s) 30. For example, the outer balloon 30b may include a plurality of protrusions (not shown) sized to be received within openings in the stents 50, e.g., annular arrangements of protrusions spaced apart from one another corresponding to the desired spacing of the stents 50 loaded onto the outer balloon. Thus, the protrusions may be received within respective openings in the stents 50, which may remain engaged together during expansion of the outer balloon 30b, e.g., due to the outer balloon 40b stretching as the outer balloon 40b and stents 50 are expanded by the inner balloon 30a, as described further elsewhere herein.

In addition or alternatively, the outer balloon 30b may include one or more features thereon for enhancing traction, friction, and/or other engagement with structures contacted by the outer balloon 30b when expanded. For example, the outer surface may be treated or textured, may include ribs or other protrusions, and the like (not shown) to increase friction or other engagement upon expansion.

Optionally, the inner and/or outer balloons 30a, 30b may include one or more features to facilitate slidable engagement or other movement of the balloons 30 relative to one another, e.g., during expansion. For example, an outer surface 39a of the inner balloon 30a and/or an inner surface 39b of the outer balloon 30b may include a lubricious coating or material, e.g., silicone, a hydrophilic material, and the like. In addition or alternatively, lubricious fluid, e.g., saline, silicone, and the like, may be provided within the space between the balloons 30. For example, a desired volume of lubricious fluid may be introduced into the interior 36b of the outer balloon 30b at any time before expanding the inner balloon 30a, e.g., via the second inflation lumen 26b. Alternatively, if the second inflation lumen 26b is eliminated, a fixed volume of lubricious fluid may be disposed within the interior 36b of the outer balloon 30b, e.g., during manufacturing, to enhance a lubricious interface between the inner and outer balloons 30a, 30b.

Such materials may allow the inner balloon 30a to unfold and/or otherwise expand without applying substantial torsional or other circumferential and/or axial forces to the outer balloon 30b and consequently to the stents 50. Thus, as the inner balloon 30a is inflated, the inner balloon 30a may apply radially outward forces against the outer balloon 30b as it expands, and consequently the stents 50, to expand the stents 50 without the outer balloon 30b transmitting non-radial forces from the inner balloon 30a to the stents 50, which may reduce the risk of migration or other unwanted movement of the stents 50.

Returning to FIGS. 1 and 2, the stents 50 may include a plurality of relatively short cylindrical or tubular rings that are each expandable from a compressed or contracted condition to an expanded condition. Although not shown, each stent 50 may include a plurality of struts configured to facilitate each stent 50 expanding, e.g., including one or more zigzag pattern of cylindrical cells (not shown). However, unlike conventional stents, each stent 50 may be relatively short, e.g., having a length between about two and twelve millimeters (2-12 mm), and only a few cells, e.g., one, two, or three cylindrical cells. In addition, each stent 50 may be decoupled or independent from the other stents 50, e.g., such that, although the stents 50 may be expanded substantially simultaneously, the expansion of a first stent 50 does not impact expansion of the other stents 50, and the stents 50 may remain decoupled and/or independent from one another after delivery. Alternatively, the apparatus 10 and systems herein may also be used to deliver a single, e.g., relatively long, stent (not shown) instead of a plurality of relatively short stents 50.

The stents 50 may be formed from plastically deformable materials capable of plastically deforming without failure within a desired range of expansion, e.g., allowing the stents 50 to expand about two to eight (2-8) times between the contracted condition and the expanded condition, e.g., from an initial diameter between about one and four millimeters (1-4 mm) to an expanded diameter between about two and twelve millimeters (2-12 mm).

Optionally, each stent 50 may include features to enhance expansion of the stent 50 in a desired manner. For example, one or both ends of each stent 50 may include cells, struts, and/or other features configured to flare outwardly relative to a central section of the stent 50. Such a configuration may accommodate expansion of the intermediate regions 37 of the outer balloon 30b relative to the stents 50, as described further below.

If desired, the stents 50 may include one or more additional features, e.g., one or more radiopaque or other markers, e.g., on each stent 50 or only on desired stents 50, e.g., the first and last stent on the balloons 30, which may facilitate positioning the stents 50 relative to a target treatment site.

During use, the apparatus 10 may be used to treat a body lumen within a patient's body, e.g., an occlusion, stenosis, or other lesion within an artery or other blood vessel. For example, the lesion may include atherosclerotic plaque or other material that partially or completely occludes blood or other fluid flow within the body lumen, and the apparatus 10 may be used to deliver a plurality of stents 50 to dilate and/or otherwise support the body lumen. In addition, the apparatus 10 may facilitate treatment of difficult-to-treat locations, e.g., curved, angulated, and/or tortuous locations within blood vessels, locations that move dynamically, e.g., cardiac vessels that may move repeatedly based on the phases of the cardiac cycle.

Initially, a guidewire (such as the guidewire 90 shown in FIG. 2) or other rail may be introduced into the patient's body until a distal end of the guidewire is disposed within a target location, e.g., across the lesion within a body lumen being treated. For example, a percutaneous puncture or cut-down may be created at a peripheral location (not shown), such as a femoral artery, carotid artery, or other entry site, and the guidewire may be advanced through the patient's vasculature from the entry site, e.g., alone or with the aid of a guide catheter (not shown) to the target location. The guide catheter may be used to advance one or more instruments (such as any of the catheters or other devices described herein) over the guidewire and into the target location.

If a lesion completely occludes a body lumen, the guidewire may be directed through the occlusion, or other devices (not shown) may be advanced over the guidewire or otherwise in conjunction with the guidewire to create a passage through the lesion for the guidewire. After the guidewire is directed into the body lumen, it may be desirable to at least partially dilate the lesion.

For example, an angioplasty catheter (not shown) may be advanced through the guide catheter and/or over the guidewire into and through the lesion, whereupon a balloon or other element on the catheter may be expanded to at least partially dilate the lesion. If desired, other procedures may also be performed at the lesion, e.g., to soften, remove, or otherwise treat plaque or other material forming the lesion, before the stents 50 are delivered. After completing any such procedures, any instruments advanced over the guidewire may be removed.

To deliver the stents 50 (or a single stent, not shown), a delivery catheter, such as the catheter 10 shown in FIGS. 1-4 may be used with the balloons 30 and stents 50 initially in contracted conditions, e.g., as shown in FIG. 3. For example, with the balloons 30 in the deflated, contracted conditions, the distal end 24 of the catheter 10 may be advanced over the guidewire 90 (shown in FIG. 2) and/or through a guide catheter (not shown) from the entry site into a target body lumen. The catheter 10 may be positioned such that the distal end 24 extends into and through the lesion, e.g., until the balloons 30 and stents 50 are centered or otherwise positioned as desired within the lesion.

The stents 50 may then be expanded and/or otherwise deployed from the catheter 10, e.g., to place the stents 50 across the lesion, e.g., spaced apart from one another within the body lumen within and on either side of the lesion.

Optionally, to facilitate positioning, the stents 50 and/or balloons 30 may be monitored using fluoroscopy or other external imaging, e.g., to observe and monitor markers (not shown) on the distal end 24, one or both balloons 30, and/or on the stents 50. For example, markers may be located on the distal end 24 to identify the ends of the substantially uniform main region 38a of the inner balloon 30a, and consequently the location of the stents 50 carried thereon.

With reference to FIGS. 2-4, the balloons 30 may be inflated or otherwise expanded to expand the stents 50 and/or dilate the body lumen. In an exemplary method, an initial expansion step may involve introducing inflation media through the second inflation lumen 26b into the interior 36b of the outer balloon 30b, e.g., to engage the outer balloon 30b and the stents 50 without substantially expanding the stents 50. For example, as shown in FIG. 2, the outer balloon 30b may be inflated to cause the regions 37 between adjacent stents 50 and/or proximal and distal to the first and last stents 50, respectively, to bulge or otherwise expand slightly. The resulting expanded regions 37 may substantially secure the stents 50 relative to one another, e.g., resisting subsequent axial movement of the stents 50.

Next, the inner balloon 30a may be inflated, e.g., causing the central region 38a to unfold and/or otherwise expand within the outer balloon 30b. As the inner balloon 30a expands, it may apply a radially outward force against the outer balloon 30b and, consequently, the stents 50. Thus, the stents 50, while remaining substantially independent from one another, may be expanded substantially simultaneously with the outer balloon 30b reducing the risk of the stents 50 migrating.

Due to the ability of the inner balloon 30a to slide relative to the outer balloon 30b, e.g., which may be enhanced by one or more coatings and/or fluid between the balloons 30, any torsional, circumferential, axial forces, and/or other non-radial forces generated by expansion of the inner balloon 30a are not transferred to the stents 50, which may otherwise cause the stents 50 to shift, slide, twist, and/or otherwise move other than expanding radially to the expanded condition.

Thus, the inner and outer balloons 30a, 30b may have different modes of expansion: the non-compliant inner balloon 30a may unfold, unroll, or otherwise unfurl, while the compliant outer balloon 30b stretches. The outer surface 39 of the non-compliant inner balloon 30a may slide along the inner surface 39b of the outer balloon 30b, e.g., with little or no twisting or other non-radial movement transferred from the inner balloon 30a to the outer balloon 30b. The outer balloon 30b, on the other hand, expands in a substantially similar manner to the stents 50, i.e., in the radial direction. Because the outer balloon 30b and the stents 50 move together, they may remain in close apposition throughout deployment. Moreover, at relatively low pressures, the compliant outer balloon may squeeze its way into the spaces between the stents and/or between individual stent struts. The resulting pattern of reciprocal engagement may secure the stents 50 in a substantially fixed position relative to the outer balloon 30b. Meanwhile, the inner balloon 30a remains free to slide against the inner surface 39b of the outer balloon 30b (e.g., due a lubricious coating and/or fluid between the inner and outer balloons 30a, 30b), e.g., to stretch or otherwise expand the outer balloon 30b, and expand the stents 50 without driving them on a collision course (e.g., down the slope of a dog-bone from ends 32, 34 of the balloons 30 towards the center regions 38). Optionally, given their similar modes of expansion, features (not shown) on the outer surface of the outer balloon 30b may mate with corresponding features on the stents 50, further minimizing the potential for movement between the two, and further securing stent position.

In an alternative embodiment, the outer balloon 30b may not be expandable independent of the inner balloon 30a. For example, the second inflation lumen 26b may be omitted, and the outer balloon 30b may be slidable around the inner balloon 30a. Thus, during inflation and consequent expansion of the inner balloon 30a, the outer balloon 30b may be stretched and/or otherwise expanded, thereby substantially simultaneously expanding the stents 50.

Once the stents 50 are fully expanded and/or deployed, the balloon(s) 30 may be deflated and/or otherwise collapsed back to the contracted conditions to facilitate removal of the catheter 10, leaving the stents 50 deployed within the target location. For example, inflation media may be evacuated from the interiors 36 of the balloons 30, e.g., substantially simultaneously or sequentially, e.g., first deflating the inner balloon 30a and then deflating the outer balloon 30b to disengage the outer balloon 30b from the expanded stents 50 or first deflating the outer balloon 30b and then deflating the inner balloon 30a.

Optionally, each stent 50 may include flarable end regions (not shown), which may be flared when the outer balloon 30b is initially inflated to engage the stents 50. In this manner, the stents 50 may become seated in annular valleys in the outer balloon 30b, which may reduce the risk of axial migration of the stents 50 relative to one another. Once the stents 50 are expanded and/or engaged with the wall of the body lumen, the outer balloon 30b may be deflated to disengage the flared ends of the stents 50, and the inner balloon 30 may optionally be inflated further to plastically deform the stents 50, e.g., into unflared substantially uniform expanded diameters.

Alternatively, the catheter 18 may be used to deliver a single, relatively long stent (not shown), which may extend along a majority of the center region 38b of the outer balloon 30b. As with delivering multiple stents, decoupling the inner and outer balloons 30a, 30b may cause the inner balloon 30a to apply radial forces to expand and/or dilate the stent, while preventing non-radial forces generated by the inner balloon 30a during unfurling or other movement to be transferred to the stent, thereby reducing the risk of a single stent being twisted or otherwise moving in an undesirable manner as the inner balloon 30a is expanded. Such decoupling may also facilitate delivering one or more stents within tortuous anatomy, e.g., such that any undesired forces generated by the inner balloon 30a during expansion within a non-cylindrical body lumen, e.g., a curved, angulated, or other vessel, may be absorbed by the interface between the inner and outer balloons 30a, 30b, rather than transferred to the stent(s) being delivered.

In yet another alternative, the outer balloon 30b may be partially inflated before introducing the distal end 24 of the catheter 10 into the patient's body. In this embodiment, the outer balloon 30b may be inflated sufficiently to engage the stents 50 (e.g., using protrusions on the outer balloon 30b, thin-walled regions 37, and/or frictional surfaces and/or materials) to prevent substantial migration while the distal end 24 is introduced into the patient's body and advanced to the target location. Once positioned where desired, the inner balloon 30a may be inflated to expand the stents 50 within the target location, e.g., similar to other embodiments herein.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. An apparatus for treating a body lumen, comprising:
    an elongate tubular member including a proximal end, a distal end sized for introduction into a body lumen, and a first inflation lumen extending between the proximal and distal ends;
    an inner balloon on the distal end formed from substantially inelastic material defining a central region, the inner balloon expandable from a delivery configuration in which the inner balloon is rolled or folded around the distal end, and an enlarged configuration in which the central region defines a substantially uniform diameter when inflation media is introduced into the first inflation lumen;
    an outer balloon on the distal end overlying the inner balloon, the outer balloon formed from elastic material such that the outer balloon expands elastically when the inner balloon is expanded from the contracted configuration to the enlarged configuration; and
    a plurality of stents disposed around an outer surface of the outer balloon and spaced apart from one another and aligned over the central region of the inner balloon.

2. The apparatus of claim 1, wherein at least one of the inner and outer balloons include one or more features to prevent substantial transfer of non-radial forces generated when the inner balloon expands from the contracted configuration to the enlarged configuration to be transferred to the outer balloon.

3. The apparatus of claim 2, wherein the outer balloon has a low friction inner surface that slidably engages an outer surface of the inner balloon during expansion of the inner balloon.

4. The apparatus of claim 2, wherein the inner balloon has a low friction outer surface that slidably engages an inner surface of the outer balloon during expansion of the inner balloon.

5. The apparatus of claim 2, wherein the one or more features comprise at least one of a lubricious coating on an outer surface of the inner balloon and a lubricious coating on an inner surface of the outer balloon.

6. The apparatus of claim 2, wherein the one or more features comprise lubricious fluid disposed within a space between the inner and outer balloons.

7. The apparatus of claim 1, wherein the outer balloon has a high friction outer surface that engages the plurality of stents to minimize movement of the stents relative to one another.

8. The apparatus of claim 1, wherein the outer balloon comprises spaced-apart features on the outer surface thereof that engage one or more stents loaded onto the outer balloon to prevent axial migration of the stents relative to the outer balloon.

9. The apparatus of claim 8, wherein the spaced-apart features comprise protrusions extending outwardly from the outer surface of the outer balloon.

10. The apparatus of claim 8, wherein the spaced-apart features comprise indentations formed in the outer balloon having shapes configured to receive one or more stents therein.

11. The apparatus of claim 1, wherein the outer balloon comprises spaced-apart features on the outer surface thereof that engage the stents to prevent axial migration of the stents relative to the outer balloon.

12. The apparatus of claim 11, wherein the spaced-apart features comprise protrusions extending outwardly from the outer surface of the outer balloon.

13. The apparatus of claim 11, wherein the spaced-apart features comprise indentations formed in the outer balloon having shapes configured to receive the stents therein.

14. The apparatus of claim 1, further comprising lubricious fluid disposed between the inner and outer balloons to facilitate the inner balloon sliding relative to the outer balloon during expansion of the inner balloon.

15. The apparatus of claim 1, wherein the tubular member comprises a second inflation lumen extending between the proximal and distal ends of the tubular member, the second inflation lumen communicating with an interior of the outer balloon for at least partially inflating the outer balloon independent of the inner balloon.

16. The apparatus of claim 1, wherein each of the plurality of stents is uncoupled from one another.

17. The apparatus of claim 1, wherein each of the plurality of stents is deployable independent of one another.

18. The apparatus of claim 1, wherein each of the plurality stents are formed from plastically deformable materials capable of plastically to expand when the inner balloon is expanded from the delivery configuration to the enlarged configuration.

19. An apparatus for treating a body lumen, comprising:
an elongate tubular member including a proximal end, a distal end sized for introduction into a body lumen, and a first inflation lumen extending between the proximal and distal ends;
an inner balloon on the distal end formed from substantially inelastic material defining a central region, the inner balloon expandable from a delivery configuration in which the inner balloon is rolled or folded around the distal end, and an enlarged configuration in which the central region defines a substantially uniform diameter when inflation media is introduced into the first inflation lumen; and
an outer balloon on the distal end overlying the inner balloon, the outer balloon formed from elastic material such that the outer balloon expands elastically when the inner balloon is expanded from the contracted configuration to the enlarged configuration,
wherein the outer balloon comprises spaced-apart features on the outer surface thereof that engage one or more stents loaded onto the outer balloon to prevent axial migration of the stents relative to the outer balloon, and
wherein the spaced-apart features comprise annular thin-walled regions of the outer balloon configured to be disposed between stents loaded on the outer balloon, the thin-walled regions having thinner wall thicknesses than regions of the outer balloon disposed under the stents.

20. An apparatus for treating a body lumen, comprising:
an elongate tubular member including a proximal end, a distal end sized for introduction into a body lumen, and a first inflation lumen extending between the proximal and distal ends;
an inner balloon on the distal end formed from substantially inelastic material defining a central region, the inner balloon expandable from a delivery configuration in which the inner balloon is rolled or folded around the distal end, and an enlarged configuration in which the central region defines a substantially uniform diameter when inflation media is introduced into the first inflation lumen;
an outer balloon on the distal end overlying the inner balloon, the outer balloon formed from elastic material such that the outer balloon expands elastically when the inner balloon is expanded from the contracted configuration to the enlarged configuration; and
a plurality of stents disposed around the outer balloon and spaced apart from one another and aligned over the central region of the inner balloon,
wherein the outer balloon comprises spaced-apart features on the outer surface thereof that engage the stents to prevent axial migration of the stents relative to the outer balloon, and
wherein the spaced-apart features comprise annular thin-walled regions of the outer balloon disposed between the stents, the thin-walled regions having thinner wall thicknesses than regions of the outer balloon disposed under the stents.

* * * * *